United States Patent [19]

Basler et al.

[11] Patent Number: 5,760,907
[45] Date of Patent: Jun. 2, 1998

[54] PROCESS AND DEVICE FOR THE OPTICAL TESTING OF A SURFACE

[75] Inventors: Norbert Basler, Hoisdorf; Jorg Fiedler, Ahrensburg; Bryan Hayes, Hamburg; Frank Hermann, Bad Oldesloe, all of Germany

[73] Assignee: Basler GmbH, Ahrensburg, Germany

[21] Appl. No.: 621,087

[22] Filed: Mar. 22, 1996

[30] Foreign Application Priority Data

Mar. 27, 1995 [DE] Germany .................. 195 11 197.4

[51] Int. Cl.$^6$ ........................................... G01B 11/00
[52] U.S. Cl. ........................................... 356/390; 350/237
[58] Field of Search .................... 356/237, 371, 356/390, 494, 445–446

[56] References Cited

U.S. PATENT DOCUMENTS

| | | | |
|---|---|---|---|
| 4,648,053 | 3/1987 | Fridge | 356/390 |
| 4,789,238 | 12/1988 | Ichikawa | 356/237 |
| 4,929,845 | 5/1990 | Amir et al. | 356/394 |
| 4,988,202 | 1/1991 | Nayar et al. | 356/394 |
| 5,058,178 | 10/1991 | Ray | 356/237 |
| 5,064,291 | 11/1991 | Reiser | 356/372 |
| 5,181,081 | 1/1993 | Suhan | 356/237 |
| 5,268,735 | 12/1993 | Hayashi | 356/237 |
| 5,497,234 | 3/1996 | Haga | 356/237 |

FOREIGN PATENT DOCUMENTS

| | | | |
|---|---|---|---|
| 0 452 905 A1 | 10/1991 | European Pat. Off. | |
| 4123916 A1 | 1/1992 | Germany | |
| 4032327 A1 | 4/1992 | Germany | |

OTHER PUBLICATIONS

Abstract of German patent DE 4032327, dated Apr. 30, 1992.

Abstract of German patent DE 4123916, dated Jan. 23, 1992.

"ITO: 3D-Meβtechnik und beleuchtungsdynamische Inspektion" (one page reference) 1993.

"Laser–Scanner–Inspektionsystem", *Kontrolle*, pp. 9–14., 1987.

*Primary Examiner*—Hoa Q. Pham
*Attorney, Agent, or Firm*—Howson and Howson

[57] ABSTRACT

A process and device for the optical testing of a surface in which the surface can be illuminated substantially from above by at least one upper light and from the side by at least one lower light, at a sharp angle with respect to the surface. The light reflected and/or scattered by the surface is recorded in a test period by at least one light-sensitive receiver and at least one actual image which is compared with at least one desired image is produced. To permit an improved test provision is made for the surface to be recorded by the light-sensitive receiver at least twice during the test period. During the recording periods in question the surface is illuminated by an at least intermittent illumination from above and/or from the side in a different manner in order to obtain at least two actual images with different illumination of the surface.

14 Claims, 4 Drawing Sheets

PROCESS AND DEVICE FOR THE OPTICAL TESTING OF A SURFACE

BACKGROUND TO THE INVENTION

The invention relates to a process for the optical testing of a surface in which the surface can be illuminated substantially from above by means of at least one upper light and from the side by means of at least one lower light, at a sharp angle with respect to the surface. In such a process the light reflected and/or scattered by the surface is recorded in a test period by at least one light-sensitive receiver and at least one actual image which is compared with at least one desired image is produced. The invention relates particularly, but not exclusively to the optical testing of the printed surface of a compact disc, upon which the following description concentrates. Nevertheless, the suitability of the invention for other surfaces will be recognised.

CDs have recently become increasingly popular as sound media for home use because of the high potential sound quality, and as pure data media in data processing because of the high potential data density. They are therefore a mass-market product, but have to meet high to very high quality demands, particularly when used as pure data media.

Generally speaking a CD comprises a circular disc, multi-layered in cross-section, with a central tap hole for fitting and centring in a player. From the bottom, i.e. viewed from the read side of the player, upwards the CD consists of a transparent plastic layer which contains all the data in the form of pits, a thin metal layer, generally of aluminium, for metallizing the plastic layer, and a thin lacquer layer which is usually hardened by UV light, for protecting the metal layer. The imprint, the so-called label, to provide information to the consumer, is then applied to the UV lacquer layer by means of known printing processes.

In the radial direction, in a CD several coaxial, circular regions which move outwards from the tap hole can be distinguished. Directly at the tap hole is the region used to fit the CD in the player. Adjoining this is a region in which the so-called ident code, by means of which the CD can be unequivocally identified, is impressed. There then follows the region used for the actual data storage. If the CD is recorded up to its maximum storage capacity the region ends directly on the outer edge region. Otherwise the so-called lead-out or a reflective strip is arranged between the edge region of the CD and the data region.

In the manufacturing process a polycarbonate blank is initially produced by the die-casting method, wherein all data are already impressed by the die. One surface of the blank is then provided with the metallic reflective layer by the sputter process and sealed with the lacquer layer. In this process the CD is centrifuged in order to achieve a uniform distribution of the lacquer layer and as thin a layer as possible. The label is then printed on the CD.

In principle the label is of no importance to the function of the CD because a CD is read from the underside. For the consumer, however, a perfect label is often a criterion for perfect playback of the CD so that it is necessary to produce a faultless print on the surface of the CD. In contrast the UV lacquer layer on a CD must always be perfect because otherwise there is the risk of the underlying metal layer oxidizing prematurely, which could cause reading errors. Processes with which the surface of the CD, i.e. the label and optionally also the UV lacquer layer, can be tested are therefore required. As a test of each CD must be performed after manufacture it is necessary to incorporate the test process for the upper side of the CD into the continuous production process. This means that there is often only a limited testing time available for the test process.

Generally speaking the surface of the CD is printed in any manner. Colour surfaces, pictures, inscriptions or the like can be applied with the most varied colour application processes for example. It is of course also possible for the CD to be partially unprinted, so that the metal layer is visible through the UV lacquer from the top. Furthermore a CD is often neither printed nor provided with a metal layer on the inner and outer edge region and is therefore transparent in those regions.

Generally speaking an optical process is used for testing the printed surface of the CD, in which the surface of the CD is photographed by a light-sensitive receiver, generally an electronic CCD camera, in the top view from above. In a data processing unit the actual image taken is compared with a previously calibrated desired image of a perfect surface with certain test criteria. Any deviation is then detected as a fault and the CD is graded according to the size and nature of the deviation.

In principle it should be noted that differently printed or unprinted regions of a CD appear different if the CD is illuminated differently. With illumination from above, the light reflected by the surface is received by the camera. Metal or reflective surfaces appear light, for example, whereas the colours remain substantially dark with this kind of illumination. When the surface of the CD is illuminated at a sharp angle from the side, the light scattered by the surface is received by the camera and the chrominance and the colour saturation can be detected.

It is evident that when a CD is tested with illumination from above only or with illumination from the side only, many imprints and hence potential deviations cannot be detected. With lateral illumination metallic surfaces appear black in the top view, and black imprints cannot be detected on them as they are only identifiable in the upper light. With illumination from above, however, colours usually appear dark in the top view, so that the colour saturation or the chrominance cannot be tested. It should also be noted that with no imprint in the data region of the CD, the pit structure, which can also be seen on the metal surface, behaves like an optical reflective grid so that a colour splitting of the lower light is caused. This means that any colour imprints of the same colour as the generally accidental colour splitting can no longer be reliably detected.

For this reason, in a known process the camera is exposed once during the test period whereas the CD is simultaneously illuminated both from above with the so-called upper light and from the side at a sharp angle with respect to the surface with the so-called lower light, and this has produced acceptable results. Simultaneous illumination with upper and lower light cannot, however, always detect some types of and faults in the print or the surface of the CD. Furthermore there is the risk that the faults which might be readily identifiable in the one light are reduced by the simultaneous illumination with the other light as far as their identifiability is concerned, so that small or low-contrast faults can barely be detected for example.

A metallic or metallized surface appears black in the lower light in the top view, for example, whereas in the upper light it appears light. This causes the actual image to take on a grey shade there, because the camera is exposed by both the one and the other light. A grey imprint with the same grey shade as this generated grey shade cannot therefore be detected and tested. Nor can the effects of the colour splitting because of the reflective grid formed by the pit structure be reliably prevented.

The consequence is that either a fault cannot be detected or a so-called pseudo-fault is indicated. This generates an unnecessary reject, however. To compensate at least partially for the mutual disturbing effect of the lighting it is also known that in order to produce the desired image, before the actual test process the printed surface of the CD is alternately illuminated by the upper light only and by the lower light only, in order to detect the metallic surfaces, the reflective surfaces or the transparent edge regions in advance, for example. The comparison between actual image and desired image can then be carried out in these regions with different criteria.

All faults cannot, however, be reliably detected in this case either. Scratches on the surface can, for example, weaken the reflected upper light whereas they intensify the scatter of the lower light in this region. This causes the scratch to appear dark in the upper light and light in the lower light, so that the scratch cannot be seen on the resulting camera picture, or can only be seen with very low contrast, and does not lead to a rejection. Nor can different types of surface roughness be detected, because a rougher surface reduces the proportion of reflected light and simultaneously increases the proportion of scattered light, so that scarcely any difference can be perceived in the picture taken by the camera.

Furthermore, with simultaneous illumination, which is often also used because of the short test time that is available, faults in the UV lacquer cannot be reliably identified. Overprinted lacquer faults in particular cannot be detected because ultimately they only cause a profile change in the CD. A profile change or a missing lacquer layer also appear light in the one light but dark in the other, however, so that here also simultaneous illumination by means of the upper light and the lower light causes a weakening of the contrast and it is no longer possible to detect the fault.

SUMMARY OF THE INVENTION

The object of the invention is therefore to provide a process and a device for the optical testing of a surface of an object with which the above-mentioned disadvantages can be avoided. A further object of the invention is to enable the process to be incorporated into the continuous production process of the object in question without problems.

According to the invention the object is achieved in that during the test period the surface is recorded at least twice by the light-sensitive receiver and during the recording times in question is illuminated by means of at least intermittent illumination from above and/or from the side in a different manner, in order to obtain at least two actual images with different illumination of the surface. The images obtained can then be compared with corresponding desired images which have also been obtained, for example, by means of corresponding illumination by the upper light and/or lower light. This has the advantage that a weakening of the contrast of certain fault phenomena or an effect on the colour reproduction due to a mixing of the reflected and the scattered light with simultaneous illumination with the upper light and the lower light can be avoided.

In particular it is possible to select the illumination in such a way that in each recording period, a certain region, a certain feature, a certain potential fault phenomenon or the like of the surface can be recorded particularly clearly and compared with a corresponding desired image. In particular, therefore, faults in the UV lacquer layer, which may even be overprinted, can also be detected because in a recording period the illumination can be selected in such a way that a weakening of the pictorial representation which is only changed by the deviating profile no longer occurs.

It can be appropriate if the illumination of the surface takes place only by the upper light or the lower light in each case in the recording periods in question. This has the advantage that the light-sensitive receiver is exposed only by the upper light in one recording period and only by the lower light in the other recording period, so that mutual influence is prevented.

It has, however, been shown that it is not possible frequently to switch the lamps of the corresponding light sources for the upper light and/or lower light on and off in the generally short test time available, which is only approx. 100 milliseconds in a test of a CD, without problems. This causes problems with halogen lamps or halide lamps in particular, because although they generate a wave spectrum that is desired for the lighting they cannot be switched on and/or off in this short time.

An embodiment of the invention can therefore provide that during the test period the surface is illuminated substantially continuously by the upper light whereas the surface is additionally illuminated by the lower light solely during at least one portion of time in at least one recording period. Alternatively provision can be made that during the test period the surface is illuminated substantially continuously by the lower light whereas the surface is additionally illuminated by the upper light solely during at least one portion of time in at least one recording period. Even if the surface of the CD has been illuminated by both the lower light and the upper light in one of the recording periods, the influence of the mutual effects can be compensated for in the data processing unit by the presence of the other actual image which had been taken with the upper light only or with the lower light only.

An advantageous embodiment of the invention provides that the upper light and the lower light bring about an exposure of the light-sensitive receiver with different intensity in each case and that the exposure times are correspondingly matched for an approximately maximum recording level of the light-sensitive receiver in the recording times in question. This has the advantage that when the CD is continuously illuminated by the lower light, for example, at a luminous intensity which causes a weaker exposure of the light-sensitive receiver, when the upper light is switched on in the second recording period, for example, in which a shorter exposure time of the light-sensitive receiver than the first exposure time is set because of the stronger upper light, the light-sensitive receiver is predominantly exposed by the light generated by the upper light. The effects due to the lower light can thus be reduced.

A particularly advantageous embodiment of the invention provides that the intensities of the illuminations in question are selected in such a way that when the surface is simultaneously illuminated by the upper light and the lower light in an exposure time of the light-sensitive receiver the one light causes an at least approximate maximum recording level of the light-sensitive receiver whereas in the same exposure time the other light causes only a fraction of the maximum recording level of the light-sensitive receiver. This has the advantage that an influence on the exposure during the exposure time in which both the upper light and the lower light illuminate the CD can be most extensively prevented by the weaker light because in the short exposure time the weaker light is scarcely able to cause an exposure of the light-sensitive receiver. It can be appropriate for the intensities of the illuminations in question to be dimensioned in such a way that the ratio of the desired exposure times by the one or other light for the maximum recording level of the light-sensitive receiver in the recording times in question is at least 1:10 to 1:200. Basically it should be borne in mind that the smaller the exposure ratio, the greater the influence from the weaker light.

Basically provision can be made that the particular illumination of the surface from above or from the side is achieved by corresponding switching on and off of corresponding light sources. It is also possible to achieve the illumination of the surface from above or from the side by covering corresponding light sources with corresponding cover means, such as mechanical elements.

It can be appropriate for flashlight to be used at least as upper light. This has the advantage on the one hand that the corresponding light can be produced in the desired time interval. On the other hand it is an advantage that flashlight in the form of a discharge lamp also produces a wave spectrum desired for illuminating the CD.

It is also appropriate that a discharge lamp, such as a halide lamp, is used at least as lower light. This is particularly advantageous when the light in question is used as constant light. The surface of the CD can be illuminated with the desired wave spectrum by means of a discharge lamp.

Basically it is advantageous when the surface is illuminated from above and/or from the side with diffuse light. This has the advantage that potential effects or erroneous assessments as a result of directly incident light are prevented.

It should be noted that the device for implementing the process according to the invention is generally incorporated into an automated device for producing and/or printing the object, such as the CD. It is therefore necessary for the CD to be moved to the mounting device of the test device and away from the mounting device by transport means. Generally speaking this means that the lower light cannot be screened with respect to the ambient area without problems, particularly not without obstructing the transport means. The lower light reflected at the CD thus shines freely into the ambient area. For this reason, a use of flashlight as lower light is generally dispensed with because this would be a considerable inconvenience to the operator because of the high light intensity and the high pulse frequency. Otherwise the lower light can also take the form of flashlight.

A preferred embodiment provides that the surface of the CD is continuously illuminated by means of the lower light and additionally at least once by means of an upper light in the form of flashlight in one of the recording periods, wherein the exposure times of the light-sensitive receiver are correspondingly set. An appropriate embodiment provides that at least the beam path of the upper light is at least partially screened with respect to the ambient area in order to prevent dazzle. The beam path of the upper light can be screened with respect to the ambient area more easily because the upper light is not arranged in the immediate vicinity of the CD. Furthermore the reflected light of the upper light does not shine freely into the ambient area but is collected in the objective of the light-sensitive receiver. In the ambient area the upper light in the form of flashlight is only perceptible because of scatter on the surface of the CD and does not therefore generally intrude.

In automatic optical test processes, electronic CCD cameras which convert the light beams received directly into an electrical signal are generally used. With these types of cameras the exposure time is set by means of corresponding control in the so-called shutter mode. This means that the camera is only light-sensitive for fractions of seconds which correspond to the exposure time. In this way, illuminations with high intensity, such as by flashlight for example, also produce correctly exposed photographs.

The conventionally used video cameras operate at 50 Hz frequency to produce a field line by line. This means that a field is present after 20 milliseconds and a frame after 40 milliseconds irrespective of the actual exposure time. To be able to produce a frame with flashlight it is necessary for the light-sensitive receiver to be exposed in both the first and in the second period to produce a field. A further embodiment of the invention therefore provides that the surface is exposed by flashlight twice during at least one recording period. This is perfectly possible within the given time frame. The distance between the flashlights is selected in such a way that in the case of a light-sensitive receiver, such as a CCD camera, which produces a frame in two successive periods for producing a field, the first flashlight falls in the first period for producing a field and the second flashlight in the second.

Producing two successive images in two recording periods thus takes approximately 80 milliseconds, whilst a test period of approx. 100 milliseconds is available. Particularly when a constant light is used, in addition to which at least one flashlight is switched on in the at least one recording period, incorporation in a continuous production process is therefore possible even when the available test period is very short.

The invention also relates to a device for the optical testing of a surface, particularly a compact disc (CD), in which the surface can be illuminated by at least one upper light substantially from above and by at least one lower light from the side at a sharp angle with respect to the surface and at least one light-sensitive receiver is provided in order to receive the light reflected and/or scattered by the surface, and in which a device is provided in order to produce at least one actual image in a test period and compare with at least one desired image. In order to be able to implement the above-mentioned process according to the invention in an advantageous manner it is provided that a first control means is provided in order to trigger the light-sensitive receiver at least twice in the test period and that a second control means is provided that is connected to the first control means and to the upper light and the lower light and thus cooperates with the first control means, that during the recording times in question the surface can be illuminated by means of an at least intermittent illumination with the upper light and/or the lower light in a different manner, in order to obtain at least two actual images with different illumination of the surface. With this device it is possible to set the desired optimum illumination during the recording periods in question by means of an alternating and/or by means of a combined illumination of the surface with the lower light and/or the upper light.

Provision can be made for the upper light or the lower light to be an intermittent light. Provision can also be made for at least the lower light to be a constant light. By this means, different illumination conditions can be produced during the recording times in question in a simple manner.

An advantageous embodiment provides that the upper light and the lower light illuminate the light-sensitive receiver with different intensity and the exposure times of the light-sensitive receiver in the recording periods are adapted according to the illumination prevailing at the time. In the different recording periods different illuminations can therefore be set in such a way that influence from the weaker light on the image taken in the exposure time of the light-sensitive receiver in which the stronger light illuminates the CD as well as the weaker light can be avoided.

The device according to the invention can provide that at least the upper light has a flashlight as the light source. Provision can also be made for at least the lower light to have a discharge lamp such as a halide lamp as the light source. The required pulse time of the intermittent light can be maintained by using flashlight. Furthermore the use of flashlight and also a discharge lamp has the advantage that the CD can be illuminated with the desired wave spectrum which at least approximately corresponds to that of daylight.

An appropriate embodiment of the invention provides that at least the beam path of the upper light is screened at least partially with respect to the ambient area by means of at least one cover element in order to prevent dazzle. This has the advantage that even when flashlight is used as the upper light, inconvenience to the operator of the production machines is extensively prevented.

BRIEF DESCRIPTION OF THE DRAWINGS

The invention will be described in greater detail below by way of example and with the aid of the accompanying diagrammatic drawings in which.

DESCRIPTION OF PREFERRED EMBODIMENTS

Figure 1:
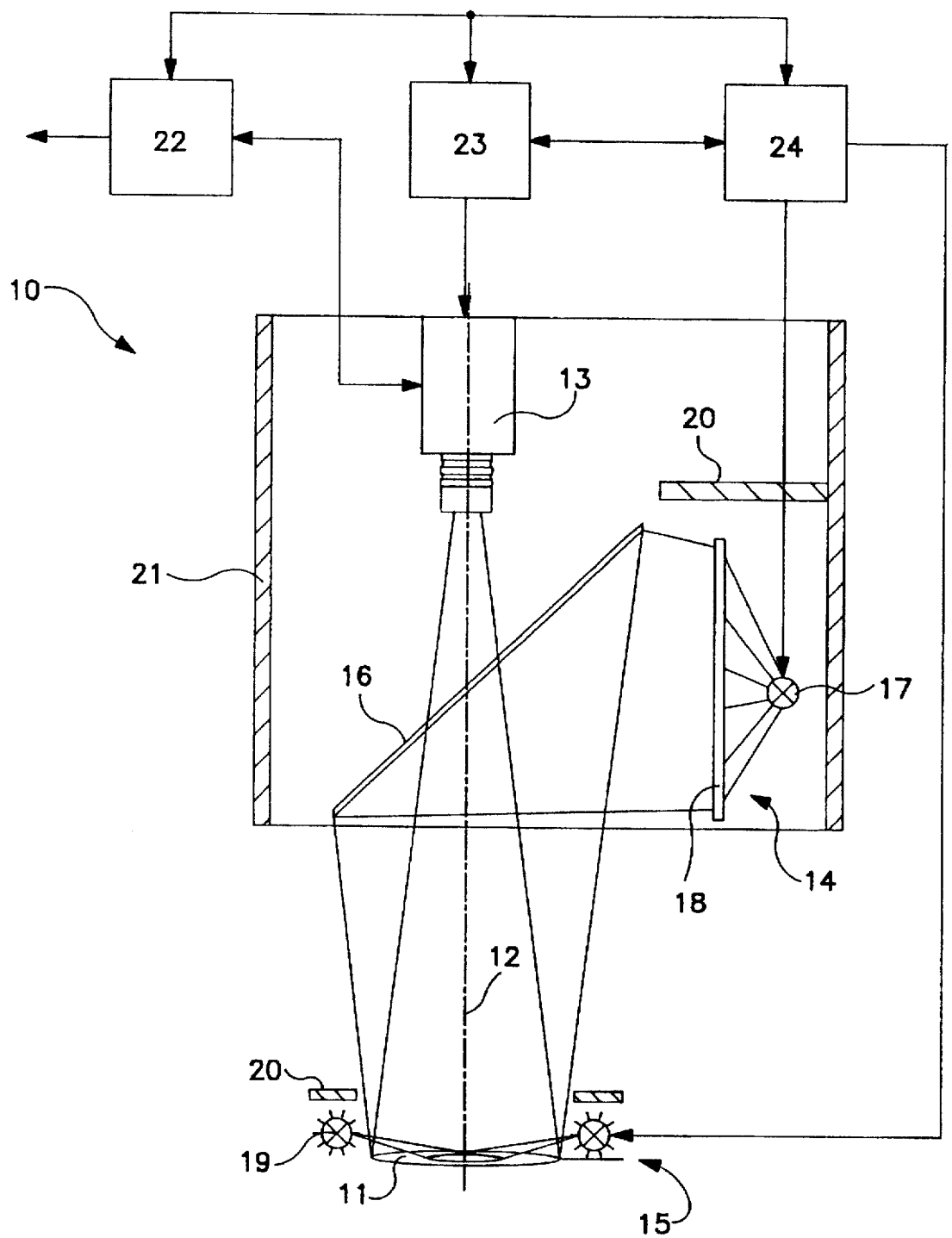
FIG. 1 shows a simplified side view of a test device.

The device 10 for the optical testing of a surface of a compact disc (CD) which is shown in FIG. 1 has a generally columnar vertical structure to which the individual functional elements are secured. For reasons of clarity the retaining devices required to secure the individual functional elements are not shown in the drawing.

In its lower section the device 10 is provided with a mounting device for a CD, which is also not shown, with which the CD 11 under test is received for the test and centred. In the upper region of the device in the direction of the longitudinal axis 12 of the device 10, which substantially corresponds to the axis of rotation of the CD 11, a light-sensitive receiver 13, such as an electronic CCD camera, is located in order to be able to photograph the surface of the CD 11 in the top view.

For the photographs by the light-sensitive receiver 13 the CD 11 can be illuminated from above by means of an upper light 14 and/or from the side at a sharp angle with respect to the surface of the CD 11 by means of a lower light 15. More specifically the arrangement in the case of the upper light 14 is such that a semi-reflecting mirror 16 is arranged between the CD 11 and the light-sensitive receiver 13 approximately in the upper half of the device 10 in such a way that the light emitted by a lateral light source 17 is reflected at the mirror 16 in the direction of the CD 11 and the CD 11 is illuminated from above. The light reflected by the CD 11 passes through the semi-reflecting mirror 16 in the direction of the light-sensitive receiver 13 and exposes it. To achieve a uniform illumination of the CD 11, a diffusor 18 is provided between the light source 17 and the semi-reflecting mirror 16. This spatial arrangement of the device has been selected in such a way that a gripping means for transporting the CD is moved to and fro between the upper light 14 and the lower mounting for the CD 11 in the continuous production process. The distance between the CD 11 and the lower edge of the unit receiving the upper light and the camera depends on the local circumstances.

In the case of the lower light 15 the arrangement is such that a substantially annular light source 19, which can also comprise several individual lamps arranged at a distance from each other in the circumferential direction, is provided laterally above in the immediate vicinity of the CD 11. This means that the CD 11 is illuminated with a light impinging at a sharp angle. The lower light 15 is aligned in such a way that only light scattered from the surface of the CD 11 can reach the light-sensitive receiver 13. The colour saturation and chrominance of the print are well accentuated by this means in particular. For uniform illumination of the CD 11, a diffusor can also be provided between the light source and the surface of the CD 11 in this case.

Corresponding cover elements 20 are provided both for the light source 17 of the upper light 14 and for the light source 19 of the lower light in order to prevent the light-sensitive receiver 13 from being directly illuminated by the light sources in question. To prevent the operator from being dazzled the upper light 14 is screened with respect to the ambient area by means of a sleeve-like cover element 21. This cover means 21 surrounds the light source 17 of the upper light 14 and the mirror 16 and can extend as far as the light-sensitive receiver 13 to prevent ambient light from influencing the image that is taken.

The output of the light-sensitive receiver 13 is connected to a data processing unit 22 in which the recorded images of the surface of the CD 11 are compared with at least one previously calibrated desired image. Depending on the test result, for example, the data processing unit 22 supplies a corresponding signal to the handling device for the CD in order to grade out a faulty CD or pass on to the rest of the production process.

The data processing unit 22 is also connected to a first control means 23 and a second control means 24, to control the different illuminations by the upper light 14 and/or the lower light 15 during the recording periods in question and to set the light-sensitive receiver 13 correspondingly. More specifically the arrangement is such that the first control means 23 is connected to the trigger of the light-sensitive receiver 13, to set its exposure times. On the one hand the second control means 24 is connected to the light source 17 of the upper light 14 and the light source 19 of the lower light 15, to switch them on and off according to the specified modes of illumination. On the other hand the control means 24 is connected to the first control means 23 to enable the illumination to be synchronized with the triggering of the light-sensitive receiver 13. It is of course also possible for the tasks of the control means 23 and 24 to be performed directly by the data processing unit 22.

Figure 2:
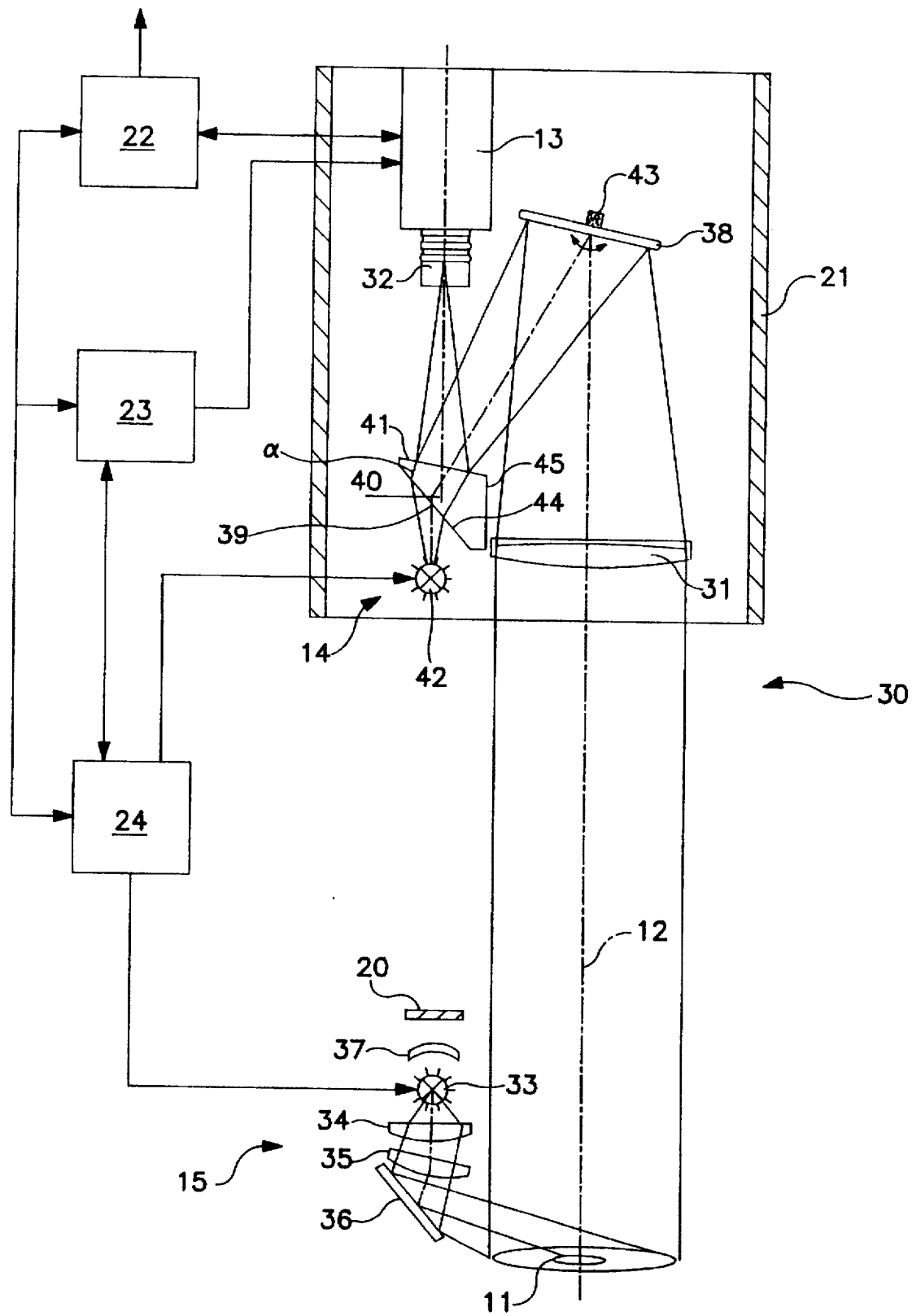
FIG. 2 shows a simplified side view of a further test device for implementing the process according to the invention.

FIG. 2 shows a further embodiment of a device 30 for the optical testing of a surface of a CD. The mode of operation of device 30 according to FIG. 2 is the same as that of device 10 according to FIG. 1, and identical elements are provided with identical reference numerals.

The substantial difference between the two devices lies in the fact that the arrangement of the light-sensitive receiver 13 and the CD 11 under test is in the form of a telecentric structure. For this purpose a lens arrangement 31, an achromatic lens for example, is provided, by means of which the CD 11 is illuminated by the upper light with substantially parallel light rays. The reflected light rays of the CD 11 are concentrated in this lens arrangement 31 and projected onto the objective 32 of the light-sensitive receiver 13. By means of this structure it is possible for the width of the device 30 to be substantially reduced compared with the width of a traditional test device. In this case the width is substantially determined by the diameter of the lens arrangement 31 which only needs to be slightly larger than the diameter of a CD or the largest width of the surface under test.

The lower light 15 can also be annular in form. It is appropriate, however, to provide the lower light on only one side of the CD 11. In this case the lower light is provided with a lens arrangement which enables the CD to be illuminated uniformly. In the embodiment shown in FIG. 2 the lower light 15 has a light source 33, a convergent lens 34, a cylindrical lens 35 and a mirror 36. A concave mirror 37 can also be provided behind the light source 33 so as better to utilize the radiated light. More specifically the arrangement is such that the light of the light source 33 is initially concentrated through the spherical convergent lens 34 and is then concentrated again through the cylindrical lens 35 in a plane into substantially parallel rays so that a pencil of rays is produced which illuminates the surface of the CD 11 with slightly convergent rays viewed from above and with substantially parallel rays viewed from the side. The order of the lenses can also be changed.

For uniform illumination provision is also made for the cylindrical lens 35 to be tiltable. By this means the constantly present lens errors can be utilized by means of a corresponding tilting with the effect that the surface of the CD 11 is illuminated with substantially identical light intensity, starting from the edge that is nearest to the lower light, as far as the edge facing away from the lower light.

Access to the handling means of the production device is substantially facilitated in that the lower light is now arranged on one side of the CD only. Furthermore the width of the test device 30 is reduced in the lower region because the illumination is no longer provided by an annular lower light which surrounds the CD laterally along its circumference and thus requires greater radial space.

By means of these measures, viz. in particular the telecentric arrangement and optionally also the use of a lower light which irradiates the CD 11 from one side only it is possible for a test device of this kind to be used in a so-called twin unit for producing CDs. In a twin unit the CDs are very close together, with an axial spacing of 135 mm for example (the diameter of a CD is 120 mm), so that when traditional units which are substantially wider in construction were used in the past, compromises always had to be accepted as regards illumination and test sharpness. It is now possible to incorporate two test devices which operate with full test sharpness and consistently faultless lighting alongside each other in the production process.

To reduce the structural height, the convergent light rays behind the lens arrangement 31 are deflected at least once before they are projected into the objective 32 of the light-sensitive receiver 13. In the embodiment shown in FIG. 2, at a mirror 38 the light rays are initially reflected downwards onto a reflecting element and then reflected upwards again towards the objective 32 of the light-sensitive receiver 13. The height of the device can be reduced by means of this double beam deflection.

The light for the upper light can be supplied, for example, by a light source which is located in the focal point of the lens arrangement 31, via a semi-reflecting mirror which is arranged in the beam path between the light-sensitive receiver 13 and the lens arrangement 31. This should be understood to mean that the focal point can of course also be displaced by corresponding beam deflections. In the embodiment shown in FIG. 2 a prism 40 whose one side 41 represents the reflecting element for the rays reflected by the CD 11 and has the form of a semi-reflecting mirror is provided to supply the light of a light source 42 for the upper light.

More specifically the prism 40 is formed in such a way that a further side 39 of the prism 40 behind the semi-reflecting mirror side 41 runs at a certain angle a to the mirror side 41 depending on the material of the prism 40. The angle a should be selected in such a way that the light rays emanating from a light source 42 are deflected onto the mirror 38 by means of a refraction at the side 39 and at the side 41 in such a way that the rays are aligned substantially parallel onto the CD 11 through the lens arrangement 31. This means that the rays converging from the lens arrangement 31 are reflected in an imaginary reverse path through the mirror 38 and are refracted at the one side 41 and the other side 39 of the prism 40 in such a way that the focal point of the lens arrangement 31 at least approximately impinges on the light source 42. Furthermore the angle is selected in such a way that the light rays emanating from the light source are refracted in such a way that they do not impinge on the objective 32 of the light-sensitive receiver 13 directly and on the other hand the light-sensitive receiver 13 cannot "see" into the light source. This means that imaginary light rays emanating from the light-sensitive receiver 13 undergo a total reflection at the inner boundary surface 44 of the side 39 of the prism 40 after the refraction at the side 41. The third side 45 of the prism 40 on which the imaginary light rays from the light-sensitive receiver are totally reflected by the boundary surface 44 can be blackened in order to prevent influence from diffuse light.

By means of this arrangement it is possible to reduce the dimensions of the device in depth also, because the light source 42 for the upper light 14 can be arranged in or close to the optical axis of the light-sensitive receiver 13 without influencing it. A lateral arrangement of the light source, such as that of the light source 17 in FIG. 1, for example, is no longer required. For uniform illumination, corresponding diffusers for the upper and/or lower light can also be provided but these are not shown for reasons of clarity.

In the embodiment shown in FIG. 2 the mirror 38 is additionally designed to be movable. This has the advantage that when calibrating the desired images for the test process, for example, the mirror 38 and hence the (light rays) reflected at the CD 11 can be displaced by a fraction, half for example, of a pixel of the light-sensitive receiver in at least one coordinate axis of the light-sensitive receiver. By this means an improvement in detection can take place in that exposure measurements of adjacent pixels can be compared with each other and/or combined in order to determine the type of surface present in that region. Grid prints, metallic prints or regions with a sharp light/dark contrast, for example, can therefore be unequivocally detected when reading-in the desired image so that a correspondingly matched comparison between the desired images and the actual images can be carried out. This can increase the test accuracy and reduce pseudo-rejects.

Basically the mirror 38 can be pivoted by any means. A piezoactuator 43 is provided in the embodiment shown in FIG. 2 because of the possible short paths and uncomplicated operation by means of an electronic control. This actuator can, for example, be provided with three rams acting on the mirror back, to move the mirror in such a way that the light rays are displaced on the light-sensitive receiver 13 approximately by a fraction of a pixel in the x-direction, y-direction and x,y direction in each case. In the rest position the mirror is pressed by a spring element against the stop face of the piezoactuator 43 so as to have a fixed position. Four images each in different viewing directions can therefore be produced in a simple manner for reading-in the desired image. The continuous test process can be carried out with the mirror stationary for example. If there is sufficient time in a continuous test process it is of course also possible to move the mirror in at least one direction in the test period.

FIGS. 3a to 3d show examples of possible modes of illumination with which the surface of the CD 11 can be illuminated differently by means of the upper light OL and/or the lower light UL within a test period TP for a CD 11 in the course of the particular recording times TA1 and TA2. The light intensity I is shown on the ordinate and the time t on the abscissa. In a graph, two abscissae for the upper light OL and the lower light UL in each case are shown over each other.

Figure 3A:
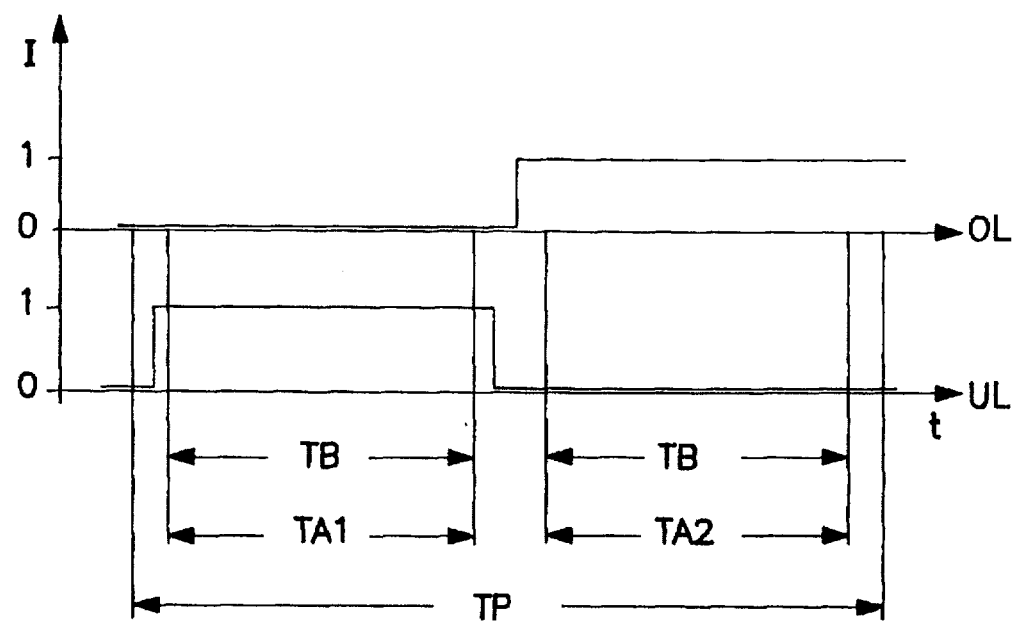
FIGS. 3a to 3d show different time sequences of the illuminations in a test period.

In FIG. 3a the surface of the CD is illuminated either by the upper light OL only or by the lower light UL only in the recording times TA1 and TA2. The images of the surface obtained in this way are free from any influence from the other light.

Figure 3B:
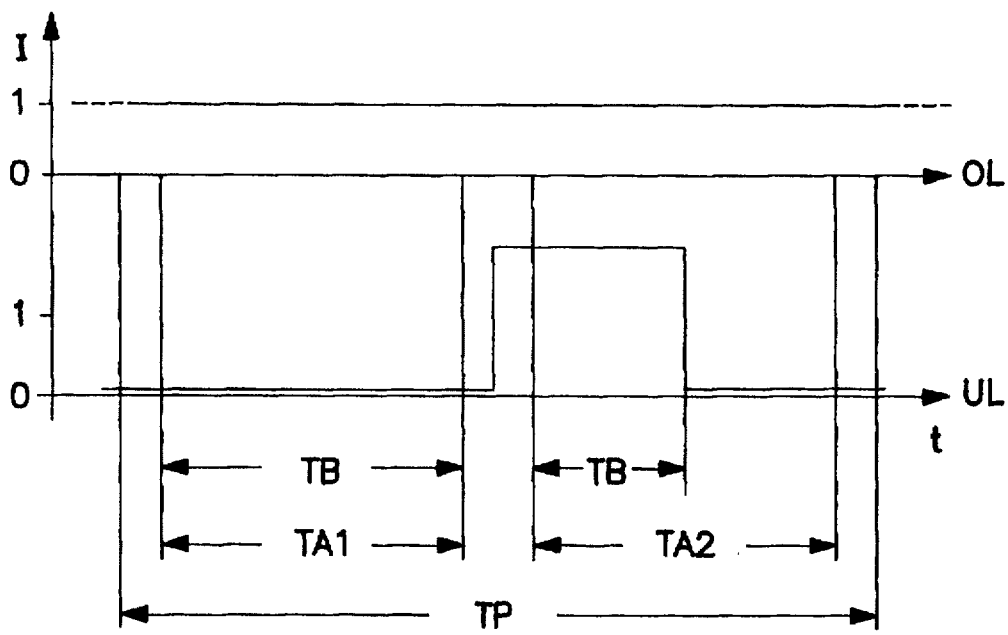

In FIG. 3b the surface of the CD is continuously illuminated by the upper light OL whereas the lower light UL is switched on with a higher intensity in the second recording period TA2.

The exposure time TB of the light-sensitive receiver 13 has therefore been made correspondingly shorter in the second recording period TA2. The higher intensity of the lower light means that the effects on the recorded image because of the simultaneous illumination of the surface by the weaker upper light OL are reduced in the course of this exposure time TB.

Figure 3C:
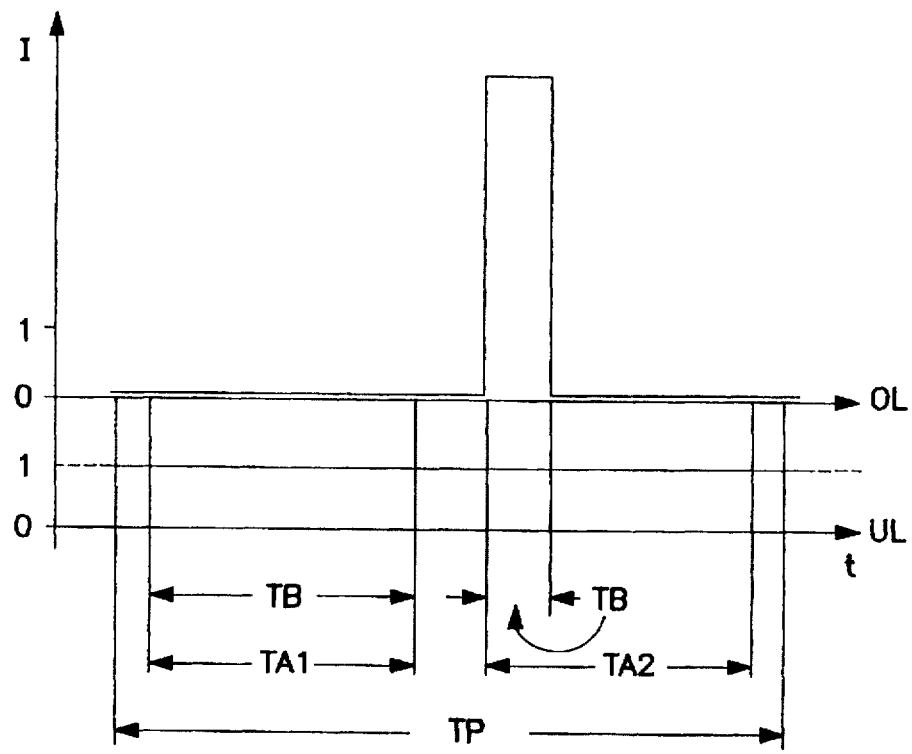

In FIG. 3c the surface is continuously illuminated by the lower light UL whereas in the second recording period TA2 the upper light OL is switched on with a substantially higher intensity I, in the form of flashlight for example. This means that the required exposure time TB of the light-sensitive receiver is reduced on the one hand and the effect of the lower light UL on the recorded image is reduced on the other hand, as the lower light brings about scarcely any additional exposure of the light-sensitive receiver 13 during the short exposure time.

An electronic CCD camera which converts the light rays received directly into an electrical signal can be used as the light-sensitive receiver. With this type of camera the exposure time is set by corresponding operation in the so-called shutter mode. This means that the camera is light-sensitive for only fractions of seconds which correspond to the exposure time.

The conventionally used video cameras operate with a 50 Hz frequency to produce a field line by line. This means that a field is present after 20 milliseconds and a frame after 40 milliseconds irrespective of the actual exposure time. In order to be able to produce a frame with flashlight it is necessary for the light-sensitive receiver to be exposed in both the first and the second period P1, P2 for producing a field.

Figure 3D:
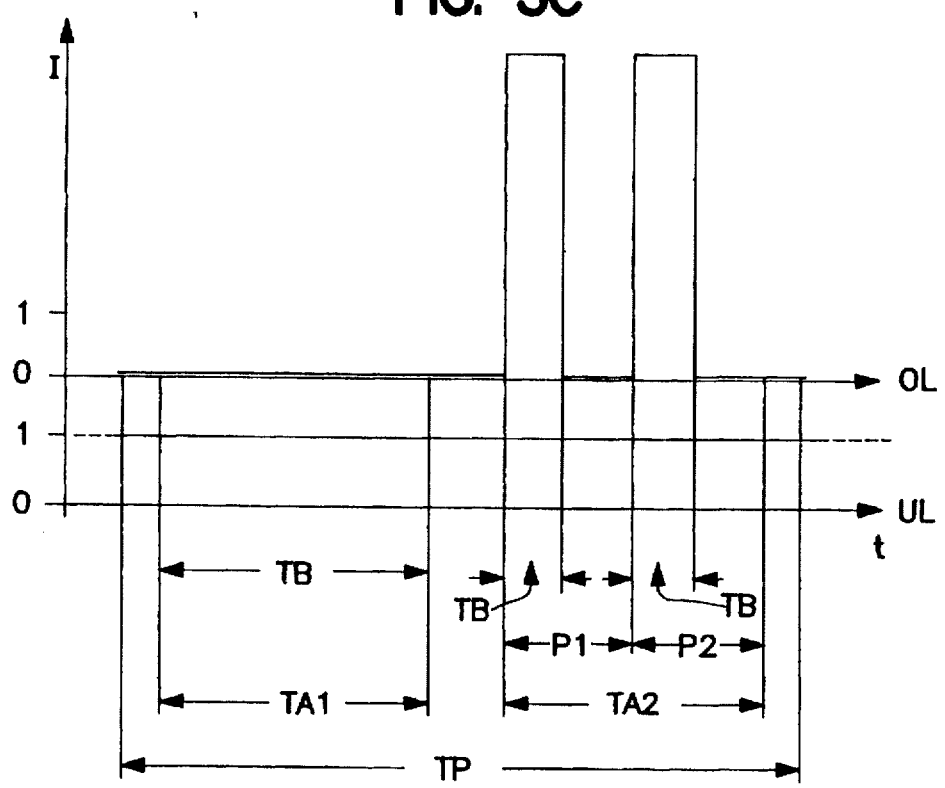

As shown in FIG. 3d, provision is therefore made for the surface to be exposed by flashlight twice during the second recording period. The interval between the flashlights is selected in such a way that the one flashlight falls in the first period and the second flashlight in the second period for producing a field P1, P2.

Producing the first image, which is generated by means of continuous exposure with the lower light, for example, takes approx. 40 milliseconds. The camera can also be light-sensitive for this entire time. In the second exposure time the camera is switched into the shutter mode and initially exposed by a flashlight, wherein the actual exposure time is 1/2000 of a second for example. After the period for producing the first field has passed after 20 milliseconds the light-sensitive receiver is exposed by the flashlight again under identical conditions. The second field is ready after a further 20 milliseconds so that the frame of the second recording period is also produced after approx. 40 milliseconds. Only approx. 80 milliseconds are therefore required to produce two successive images whereas a test period of approx. 100 milliseconds is available.

In the modes of operation shown in FIGS. 3a to 3d it was assumed that the flashlight is fired in the second exposure time for example. It is of course also possible for this to take place in the first recording. Furthermore, the start of the exposure time TB for the light-sensitive receiver and the start of the particular recording periods TA1 and TA2 coincide in FIGS. 3a–d. It is of course also possible for the exposure times to be basically shorter than the recording times on the one hand and/or to start at a different time from the recording times on the other hand. Furthermore, so-called dead times are provided bewteen the recording periods and also between the test periods. These dead times substantially depend on the performance characteristics of the light-sensitive receiver. It is of course also possible for the recording times and also the test times to follow each other immediately.

It is evident that an improved test of a surface can take place by means of the process and with the device according to the invention. In particular, two images of the surface under test can be produced, one of which was taken substantially with the light reflected by the surface only and the other with the light scattered by the surface only. Upper light and lower light are correspondingly aligned so that the light-sensitive receiver substantially receives the light of the upper light reflected at the surface and/or the light of the lower light scattered by the surface.

Even if an image has been produced with illumination by both the upper light and the lower light, however, with the aid of the other image the corresponding portion of light can be separated and compensated for in the data processing unit for evaluation purposes. If illumination takes place by upper and lower light, one of which brings about a substantially more intensive exposure of the light-sensitive receiver, this compensation is not absolutely necessary.

List of Reference Numerals

10 Device
11 CD
12 Axis
13 Light-sensitive receiver
14 Upper light
15 Lower light
16 Semi-reflecting mirror
17 Light source
18 Diffusor
19 Light source
20 Cover element
21 Cover element
22 Data processing unit
23 First control means
24 Second control means
30 Device 31 Lens arrangement
32 Objective
33 Light source
34 Lens
35 Cylindrical lens
36 Mirror
37 Concave mirror
38 Mirror
39 Side
40 Prism
41 Mirror side
42 Light source
43 Piezoactuator
44 Boundary surface

We claim:

1. A process for the optical testing of a surface of a compact disc, said process comprising the steps of:
   arranging a light-sensitive receiver above the surface in order to obtain a top view of the surface,
   illuminating the surface during a first recording time of the light-sensitive receiver from substantially above by at least one upper light such that only light reflected by the surface exposes the light-sensitive receiver in order to obtain a first picture of the surface comprising only light reflected from the surface,
   illuminating the surface during a second recording time of the light-sensitive receiver at a sharp angle with respect to the surface by a lower light aligned such that only light scattered from the surface exposes the light-sensitive receiver in order to obtain a second picture of the surface comprising only light scattered from the surface for controlling the surface's chrominance and color saturation, and
   comparing the first and the second picture with corresponding desired pictures;
   wherein the surface is illuminated by both the upper light and the lower light only during one of the recording times; and
   wherein the surface is substantially continuously illuminated by the lower light during both the recording times whereas the surface is additionally illuminated by the upper light during one of the recording times.

2. A process according to claim 1, wherein the upper light is a flashlight.

3. A process for the optical testing of a surface of a compact disc, said process comprising the steps of:
   arranging a light-sensitive receiver above the surface in order to obtain a top view of the surface,
   illuminating the surface during a first recording time of the light-sensitive receiver from substantially above by at least one upper light such that only light reflected by the surface exposes the light-sensitive receiver in order to obtain a first picture of the surface comprising only light reflected from the surface,
   illuminating the surface during a second recording time of the light-sensitive receiver at a sharp angle with respect to the surface by a lower light aligned such that only light scattered from the surface exposes the light-sensitive receiver in order to obtain a second picture of the surface comprising only light scattered from the surface for controlling the surface's chrominance and color saturation, and
   comparing the first and the second picture with corresponding desired pictures;
   wherein the surface is illuminated by both the upper light and the lower light only during one of the recording times; and
   wherein the surface is substantially continuously illuminated by the upper light during both the recording times whereas the surface is additionally illuminated by the lower light during one of the recording times.

4. A process for the optical testing of a surface of a compact disc, said process comprising the steps of:
   arranging a light-sensitive receiver above the surface in order to obtain a top view of the surface,
   illuminating the surface during a first recording time of the light-sensitive receiver from substantially above by at least one upper light such that only light reflected by the surface exposes the light-sensitive receiver in order to obtain a first picture of the surface comprising only light reflected from the surface,
   illuminating the surface during a second recording time of the light-sensitive receiver at a sharp angle with respect to the surface by a lower light aligned such that only light scattered from the surface exposes the light-sensitive receiver in order to obtain a second picture of the surface comprising only light scattered from the surface for controlling the surface's chrominance and color saturation, and
   comparing the first and the second picture with corresponding desired pictures;
   wherein the surface is illuminated by both the upper light and the lower light only during one of the recording times; and
   wherein the upper light and the lower light effect an exposure of the light-sensitive receiver with difference intensities, and that the intensities are selected so that when the surface is illuminated by both the upper light and the lower light in an exposure time of the light-sensitive receiver, one of the upper and lower lights causes an approximate maximum recording level of the light-sensitive receiver whereas in the same exposure time the other light causes only a fraction of the maximum recording level of the light-sensitive receiver.

5. A process according to claim 4, wherein the intensities of the illumination are dimensioned such that the required exposure times by the one light or the other light for the maximum recording level of the light-sensitive receiver is about 1:10 to 1:200.

6. A process according to claim 4, wherein the lower light is a discharge lamp and the upper light is a flashlight.

7. A device for the optical testing of a surface of a compact disc, said device comprising:
   a light-sensitive receiver arranged above the surface to get a top view of said surface,
   an upper light adapted to illuminate the surface from above in order to expose the light-sensitive receiver only with light reflected by said surface,
   a lower light adapted to illuminate the surface at a sharp angle and aligned with respect to said surface such that only light scattered by said surface exposes the light-sensitive receiver,
   first control means for triggering the light-sensitive receiver for at least a first recording time and a second recording time during one test period in order to produce a first and a second picture of the surface,
   second control means connected to the first control means and to the upper light and lower light, said second control means being adapted to switch the upper light and the lower light during said test period such that the surface is illuminated during the first recording time by both the lower and the upper light in order to obtain the first picture of said surface comprising only light reflected from the surface, and such that the surface is illuminated during the second recording time by only the lower light in order to obtain the second picture of said surface comprising only light scattered from the surface for controlling chrominance and color saturation of the surface, and an apparatus for comparing the first and the second picture with corresponding desired pictures.

8. A device according to claim 7, wherein the lower light is a continuous light whereas the upper light is an intermittent light.

9. A device according to claim 8, wherein the upper light is a flashlight.

10. A device according to claim 7, wherein the upper light and the lower light illuminate the light-sensitive receiver with different intensity and the exposure times of the light-sensitive receiver in the recording times are adapted to said intensities.

11. A device according to claim 10, wherein the upper light is a flashlight.

12. A device according to claim 7, wherein the upper light is a flashlight.

13. A device for the optical testing of a surface of a compact disc, comprising:

a light-sensitive receiver arranged above the surface to get a top view of said surface;

an upper light adapted to illuminate the surface from above in order to expose the light-sensitive receiver only with light reflected by said surface;

a lower light adapted to illuminate the surface at a sharp angle and aligned with respect to said surface such that only light scattered by said surface exposes the light-sensitive receiver, first control means for triggering the light-sensitive receiver for at least a first recording time and a second recording time during one test period in order to produce a first and a second picture of the surface, second control means connected to the first control means and to the upper light and lower light, said second control means being adapted to switch the upper light and the lower light during said test period such that the surface is illuminated during the first recording time by the upper light in order to obtain the first picture of said surface comprising only light reflected from the surface, and such that the surface is illuminated during the second recording time by the lower light in order to obtain the second picture of said surface comprising only light scattered from the surface for controlling chrominance and color saturation of the surface; and an apparatus for comparing the first the second picture with corresponding desired pictures;

wherein the upper light and the lower light illuminate the light-sensitive receiver with different intensity and the exposure times of the light-sensitive receiver in the recording times are adapted to said intensities; and wherein the difference of the intensities is such that in one exposure time of the light-sensitive receiver, one of the upper and lower lights effects an approximate maximum recording level of the light-sensitive receiver whereas in the same exposure time the other of the upper and lower lights effects only a fraction of the maximum recording level of the light-sensitive receiver.

14. A device according to claim 13, wherein the intensities of the illumination are dimensioned such that a ratio of the required exposure time by the one or the other light for the maximum recording level of the light-sensitive receiver is about 1:10 to 1:200.

* * * * *